United States Patent [19]
Yamazaki et al.

[11] Patent Number: 5,247,117
[45] Date of Patent: Sep. 21, 1993

[54] PROCESS FOR REMOVING ACIDIC IMPURITIES FROM ALKOXYSILANES

[75] Inventors: Toshio Yamazaki; Masaaki Yamaya, both of Annaka; Hideyoshi Yanagisawa, Gunma; Masayuki Takahashi, Annaka, all of Japan

[73] Assignee: Shin-Etsu Chemical Co., Ltd., Tokyo, Japan

[21] Appl. No.: 791,652

[22] Filed: Nov. 13, 1991

[30] Foreign Application Priority Data

Nov. 13, 1990 [JP] Japan .................. 2-308391

[51] Int. Cl.$^5$ .................. C07F 7/70
[52] U.S. Cl. .................. 556/466
[58] Field of Search .................. 556/466

[56] References Cited

U.S. PATENT DOCUMENTS

| | | | |
|---|---|---|---|
| 3,316,267 | 6/1974 | Chuang | 203/8 |
| 4,774,347 | 9/1988 | Marko et al. | 556/466 |
| 4,924,022 | 5/1990 | Bank et al. | 556/471 |
| 4,927,948 | 5/1990 | Bernhardt et al. | 556/401 |
| 4,956,486 | 9/1990 | Marko et al. | 556/466 |
| 4,962,221 | 10/1990 | Huntress et al. | 556/466 X |
| 5,104,999 | 4/1992 | Satoh | 556/466 |

FOREIGN PATENT DOCUMENTS

| | | |
|---|---|---|
| 0162390 | 11/1985 | European Pat. Off. |
| 0361325 | 4/1990 | European Pat. Off. |
| 2238295 | 1/1973 | Fed. Rep. of Germany |
| 0278726 | 8/1988 | Fed. Rep. of Germany |
| 60-16996 | 1/1985 | Japan |

*Primary Examiner*—Paul F. Shaver
*Attorney, Agent, or Firm*—Lowe, Price, LeBlanc & Becker

[57] ABSTRACT

A process for removing acidic impurities from alkoxysilanes obtained from halogenosilanes and alcohols which inevitable contain small amounts of acidic impurities is described. In the process, at least one member selected from alkali metal salts of alcohols and amines having a great steric hindrance as having a bulky substituent is added to the alkoxysilane for a time sufficient to neutralize the acidic impurities and the mixture is purified by distillation to obtain a substantially acidic impurity-free alkoxysilane.

11 Claims, No Drawings

PROCESS FOR REMOVING ACIDIC IMPURITIES FROM ALKOXYSILANES

BACKGROUND OF THE INVENTION

1. Field of the Invention

This invention relates to a process for preparing alkoxysilanes and more particularly, to a process for removing inevitable acidic impurities from organic functional alkoxysilanes to obtain substantially acidic impurity-free alkoxysilanes.

2. Description of the Prior Art

It is usual to prepare alkoxysilanes by a process wherein halogenosilanes such as chlorosilanes, bromosilanes, iodosilanes and the like are esterified with alcohols. The alkoxysilanes obtained by the process inevitably contain halogen-containing components, which are difficult to remove by purification through distillation. The presence of the acidic impurities even in small amounts is disadvantageous in that when the alkoxysilane is directly applied onto metal surfaces as a silane coupling agent or even when it is used in the neighbourhood of metals, the impurities cause the metal to be corroded and degrade storage stability because the alkoxy groups are liable to be hydrolyzed by the action of the impurities. In addition, such impurities will bring about changes in quality with time after molding and curing of the alkoxysilane.

For instance, there is known a technique of preparing so-called water-crosslinking resins which are obtained by subjecting alkoxysilanes to grafting with polyolefins or acrylic resins or copolymerization with olefins or acrylic monomers. If alkoxysilanes containing small amounts of acidic impurities are used for this purpose as they are, the resultant water-crosslinking resin undergoes crosslinkage during storage with the possibility that the molding is not possible or the resin is gelled. This is because the acidic impurities contained in the alkoxysilane serve as a catalyst for hydroysis of the alkoxy groups.

In order to overcome the above disadvantages, there have been proposed several methods of removing the small amount of acidic impurities from the alkoxysilanes. Such methods include (1) a method wherein agents for catching up halogen-containing components such as tertiary amines or urea are used for re-esterification, (2) a method using sodium alkoxides for neutralization, and (3) a method wherein epoxy compounds are reacted to catch up the acidic impurities.

However, the re-esterification method (1) is disadvantageous in that because the produced salts are soluble, the acidic impurities cannot be completely removed even when the re-esterification procedure is repeated several times. With the neutralization method (2), although the small amounts of acidic impurities can be removed efficiently, this method cannot be applied to alkoxysilanes having functional groups, such as an acrylic or methacrylic group and an epoxy group, which are liable to undergo nucleophilic reaction. Further, with the method (3) using the reaction with an epoxy group, halogen atoms are taken in the intended alkoxysilane, with the attendant problems with respect to the degradation with time and the purity after purification.

SUMMARY OF THE INVENTION

It is accordingly an object of the invention to provide a process for removing acidic impurities from alkoxysilanes which inevitably contain such impurities, thereby obtaining substantially acidic impurity-free alkoxysilanes.

It is another object of the invention to provide a process for substantially completely removing acidic impurities from alkoxysilanes irrespective of the type of alkoxysilane.

The invention is based on the finding that when alkali metal salts of alcohols or amines having a great steric hindrance are added to organic functional alkoxysilanes which inevitably contain acidic impurities, the salt selectively reacts with and neutralize the acidic impurities and the thus neutralized impurities can be readily removed by distillation without adverse influence on the organic functional alkoxysilane.

According to the present invention, there is provided a process for efficiently removing acidic impurities from alkoxysilanes, which comprises:

providing an organic functional alkoxysilane of the following general formula which inevitably contains small amounts of acidic impurities

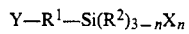

wherein Y represents an organic functional group, X represents an alkoxy group having from 1 to 4 carbon atoms, $R^1$ represents a divalent hydrocarbon group having from 1 to 11 carbon atoms, $R^2$ represents a monovalent hydrocarbon group having from 1–6 carbon atoms, and n is a value of 1, 2 or 3;

adding, to the alkoxysilane, at least one member selected from the group consisting of alkali metal salts of alcohols and amines each having a great steric hindrance until substantially all of the acidic impurities are neutralized with the at least one member; and subjecting the resulting mixture to distillation to remove the neutralized acidic impurities from the alkoxysilane to obtain a substantially acidic impurity-free alkoxysilane.

EMBODIMENTS AND DETAILED DESCRIPTION OF THE INVENTION

The alkoxysilanes used in the process of the invention are organic functional alkoxysilanes of the general formula, $Y-R^1-Si(R^2)_{3-n}X_n$, wherein Y represents an organic functional group, X represents an alkoxy group having from 1 to 4 carbon atoms, $R^1$ represents a divalent hydrocarbon group having from 1 to 11 carbon atoms, $R^2$ represents a monovalent hydrocarbon group having from 1 to 6 carbon atoms, and n is a value of 1, 2 or 3.

In the formula, specific examples of the organic functional group represented by Y include an alkenyl group having from 2 to 10 carbon atoms, an alkynyl group having from 2 to 10 carbon atoms, an epoxy group, an acrylic group, a methacrylic group, an amino group, a halogen atom, a mercapto group, a hydroxyl group, a cyano group, an isocyanate group, a thiocyanate group, an amido group, a ureido group, a sulfido group, a carboxyl group or the like. If n is 2 or 3, X's may be the same or different. Each X represents an alkoxy group having from 1 to 4 such as, for example, a methoxy group, an ethoxy group, a n-propoxy group, an iso-propoxy group, an iso-propenoxy group, a n-butoxy group, an iso-butoxy group, a tert-butoxy group and the like. $R^1$ is a divalent hydrocarbon group having from 1 to 11 carbon atoms and specific examples include a linear or cyclic alkylene group. In addition, the divalent hydrocarbon group may be branched and may contain an arylene group such as a phenylene group. If n is 1, $R^2$'s may be the same or different and represent a monovalent hydrocarbon group having from 1 to 6 carbon atoms and specific examples include an alkyl group such as a methyl group, an ethyl group, a propyl group, a butyl group and the like, and a phenyl group. n is an integer of 1, 2 or 3.

The process of the invention is most effective when the organic functional alkoxysilanes have an acrylic or methacrylic group as Y. Examples of such alkoxysilanes include γ-methacryloxypropyltrimethoxysilane, γ-methacryloxypropylmethyldimethoxysilane, γ-methacryloxypropyldimethylmethoxysilane, γ-methacryloxypropyltriethoxysilane, γ-methacryloxypropylmethyldiethoxysilane, γ-methacryloxypropyldimethylethoxysilane, γ-acryloxypropyltrimethoxysilane, γ-acryloxypropylmethyldimethoxysilane, γ-acryloxypropyldimethylmethoxysilane, γ-acryloxypropyltriethoxysilane, γ-acryloxypropylmethyldiethoxysilane, γ-acryloxypropyldimethylethoxysilane, methacryloxymethyltrimethoxysilane, methacryloxymethylmethyldimethoxysilane, methacryloxymethyldimethylmethoxysilane, methacryloxymethyltriethoxysilane, methacryloxymethylmethyldiethoxysilane, methacryloxymethyldimethylethoxysilane, acryloxymethyltrimethoxysilane, acryloxymethylmethyldimethoxysilane, acryloxymethyldimethylmethoxysilane, acryloxymethyltriethoxysilane, acryloxymethylmethyldiethoxysilane, acryloxymethyldimethylethoxysilane and the like.

The organic functional alkoxysilanes which are provided as a starting material in the practice of the invention and which inevitably contain small amounts of acidic impurities are those which are prepared by esterification between halogenosilanes and alcohols as set out hereinbefore in the prior art. In this process, acidic impurities based on the halogen in the halogenosilane are inevitably contained in the alkoxysilane crude product. As a matter of course, any other processes of preparing alkoxysilanes wherein acidic impurities are secondarily produced may be used to provide the starting organic functional alkoxysilane. For example, organic acids such as acrylic acid or methacrylic acid may be contained as the acidic impurity in the alkoxysilanes. Such organic acids may derived from starting materials or may be formed through decomposition during the reaction or distillation. In the practice of the invention, removal of both types of acidic impurities is intended. In general, the acidic impurities are formed in amounts of from 1 to 10,000 ppm.

In order to remove the inevitable acidic impurities from the alkoxysilane product, alkali metal salts of alcohols or amines having a great steric hindrance are added to the alkoxysilane product. The alkali metal salt serves as a neutralizing agent for the acidic impurities contained in an intended alkoxysilane. The alcohols or amines of the alkali metal salts are preferably those of the following formulas

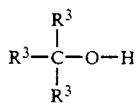
(a)

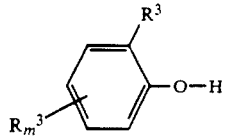
(b)

(c)

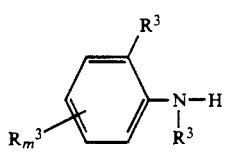
(d)

in which $R^3$'s may be the same or different and represent a monovalent hydrocarbon group having from 1 to 10 carbon atoms, and m is a value of 0, 1, 2, 3 or 4. [Examples of the monovalent hydrocarbon group include an alkyl group having from 1 to 10 carbon atoms or an unsubstituted or substituted phenyl group having up to 10 carbon atoms.]

More preferably, the alcohol or amine moiety in the alkali metal salts should have at least one structure of the following formula (I)

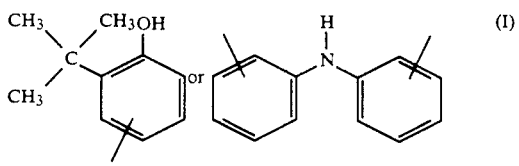
(I)

These metal salts are derived from alcohols or amines having a bulky substituent in the vicinity of or joined to the oxygen or nitrogen atom. Such a bulky substituent includes a benzene ring.

Specific examples of the neutralizing agent include alkali metal salts of phenols such as 2-tert-butylphenol, 2-tert-butyl-p-cresol, 2-tert-butyl-p-anisole, 2,6-di-tert-butylphenol, 2,6-di-tert-butyl-p-cresol, 2,6-di-tert-butyl-4-ethylphenol and the like, bis or trisphenols such as 2,2'-methylenebis(4-methyl-6-tert-butylphenol), 2,2'-methylenebis(4-ethyl-6-tert-butylphenol) and the like, and anilines such as N,N-diphenylamine, N-phenyl-p-methylaniline, N,N-di(4-methylphenyl)amine, phenoxazine, phenothiazine and the like. In addition, 2,4,6-tris-(2',4'-tert-butyl-3'-hydroxybenzyl)mesitylene may also be used, if desired. The alkali metals include sodium, potassium and the like The neutralizing agent can be readily obtained by reaction, in solvents, of alkali metal alkoxides whose alkoxide moiety has from 1 to 4 carbon atoms or alkali metals with alcohols or amines having a great steric hindrance as set out above. The solvent used in the above reaction is selected to make a homogeneous reaction system. The reaction is not critical and may be carried out by known techniques. For instance, an alkali metal alkoxide solution is dropped in a solution of an alcohol or amine having a great steric hindrance, by which the reaction proceeds rapidly and stoichiometrically, thereby obtaining an intended neutralizing agent. Care should be paid to the fact that if the alkali metal alkoxide having a great nucleophilic property is left unreacted, it will cause unfavorable side reactions with alkoxysilanes. The thus obtained neutralizing agent will produce reaction species with high nucleophilicity through an equilibrium reaction when coexisting with a secondarily produced alcohol or moisture in air. Accordingly, the neutralizing agent should be used in a dried and finely divided state, or should be used after removal of the alcohol or moisture to a satisfactory extent.

Organic functional alkoxysilanes which are treated according to the process of the invention are usually subjected to purification by distillation. For the elimination by neutralization of small amounts of acidic impurities from the alkoxysilane, it is preferred to effect the neutralization with the agent immediately before the distillation. More particularly, the reaction system of alkoxysilanes containing a solvent for the reaction may be directly subjected to the neutralization. Alternatively, the reaction system may be once subjected to rough distillation to remove a substantial amount of the solvent therefrom, followed by the neutralization. Subsequently, the neutralized solution is subjected to precise distillation to obtain substantially impurity-free alkoxysilanes.

The amount or concentration of the neutralizing agent and the temperature and time for the neutralization are not critical. These conditions may vary depending on the history or type of alkoxysilane. The neutralizing agent is preferably added in an amount of from 0.1 to 2 wt % based on the effective alkoxysilane ingredient irrespective of whether rough distillation is effected or not. The neutralization is preferably carried out at a temperature of from room temperature to 80° C. for 1 to 2 hours under agitation. If the alkoxysilane to be neutralized contains an alcohol or moisture, reaction species which exhibit great nucleophilicity are formed through the equilibrium reaction between the neutralizing agent and the alcohol or moisture. Prior to the neutralization, the alcohol or moisture should be removed from the alkoxysilane to a satisfactory extent. In order to prevent moisture in air from entering the neutralization system during the treatment, the neutralization should preferably be effected in a stream of nitrogen.

The neutralizing agent used in the process of the invention has strong basicity but is very weak in nucleophilicity because of the steric hindrance. According, if the agent is added in excess, it does not adversely influence the alkoxysilane. In this connection, however, an excess agent may be removed by adsorption with an adsorbent or by distillation after addition of alkali metal scavengers. If precipitates such as salts are settled by the neutralization treatment, they should preferably be removed by filtration, if necessary, after which the alkoxysilane is purified by distillation. These salts are, in most cases, inorganic in nature, so that if the neutralization system is subjected to distillation without removal of the precipitated by filtration, such precipitates will be left merely as a residue.

The thus neutralized alkoxysilane can be purified by distillation by any ordinary procedure. The resultant alkoxysilane is detected with no trace acidic impurities which would be otherwise contained in prior art processes.

The alkoxysilane obtained according to the process of the invention can be subjected to graft polymerization with polyolefins or acrylic resins or copolymerization with olefins or acrylic monomers. Examples of the polyolefins and acrylic resins include polymers or copolymers of ethylene, propylene, butadiene, styrene, acrylic acid or its esters, methacrylic acid or its esters, and the like. Further, these monomers are used for copolymerization of the alkoxysilane.

For example, water-crosslinkable polyethylene which is obtained by copolymerization of ethylene and γ-methacryloxypropyltrimethoxysilane is particularly described.

The water-crosslinkable polyethylene is a thermoplastic resin which has a polyethylene backbone having trimethoxysilyl groups bonded at side chains thereof. This resin is usually preserved in the form of powder, pellets or tablets, and is thermally melted or softened when used and molded. The resultant molding is crosslinked in boiling water or in an atmosphere of steam to obtain a final product. The thus water-crosslinked polyethylene is not deformed when heated to a temperature at which ordinary polyethylene is softened and deformed. However, if the starting γ-methacryloxypropyltrimethoxysilane contains small amounts of acidic impurities as in prior art, such impurities serve as a catalyst. As a consequence, during the preservation in the form of powder or the like, the crosslinkage is caused to proceed through hydrolysis and condensation reaction of the methoxy groups. If heated, such a resin is not melted or softened, making it impossible to mold.

According to the invention, the alkoxysilanes which are substantially free of any acidic impurities can be readily obtained without needing any substantial variation or change of existing apparatus or steps. When the alkoxysilane is applied as water-crosslinking resins, the storage stability can be remarkably improved.

The present invention is more particularly described by way of examples, which should not be construed as limiting the invention.

Preparation of neutralizing agents is first described in the following references.

REFERENCE 1

22.0 g (0.1 mole) of 1,6-di-tert-butyl-p-cresol was dissolved in 100 g of toluene, in which 19.3 g (0.1 mole) of a methanol solution of 28% sodium methoxide was dropped, followed by agitation at room temperature for 1 hour and removal of the solvent by distillation under reduced pressure. The resultant purple solid was broken into fine pieces to obtain pink neutralizing agent A.

REFERENCE 2

36.8 g (0.1 mole) of 2,2'-methylenebis(4-ethyl-6-tert-butylphenol) was dissolved in 100 g of toluene, in which 19.3 g (0.1 mole) of a methanol solution of 28% sodium methoxide was dropped, followed by agitation at room temperature for 1 hour and removal of the solvent by distillation under reduced pressure. The resultant green solid substance was broken into pieces to provide yellowish green neutralizing agent B.

REFERENCE 3

The general procedure of Reference 2 was repeated except that 38.6 g (0.2 moles) of the methanol solution of 28% sodium methoxide was used, thereby obtaining greenish yellow powdery neutralizing agent B'.

REFERENCE 4

38.7 g (0.05 moles) of 2,4,6-tris(2',4'-tert-butyl-3'-hydroxybenzyl)mesitylene was dissolved in 100 g of toluene, in which 9.7 g (0.05 moles) of a methanol solution of 28% sodium methoxide was dropped, followed by agitation at room temperature for 1 hour and removal of the solvent by distillation under reduced pressure. The resultant dark red solid substance was broken into fine pieces to obtain neutralizing agent C in the form of an yellowish red powder.

REFERENCE 5

The general procedure of Reference 4 was repeated except that the amount of the methanol solution of 28% sodium methoxide was 14.5 g (0.075 moles), thereby obtaining neutralizing agent C' in the form of an orange powder.

REFERENCE 6

The general procedure of Reference 4 was repeated except that the amount of the methanol solution of 28% sodium methoxide was 29.0 g (0.15 moles), thereby obtaining neutralizing agent C" in the form of a dark red powder.

EXAMPLE 1

Trichlorosilane and allyl methacrylate were subjected to hydrosilylation addition reaction in a solvent in the presence of a platinum catalyst, followed by esterification reaction with methanol and urea. After removal of urea hydrochloride from the resultant reaction solution, low boiling components including the solvent were distilled off from the solution under reduced pressure to obtain crude γ-methacryloxypropyltrimethoxysilane having a purity of approximately 90%.

20 g of neutralizing agent B obtained in Reference 2 was added to 2 kg of the thus obtained crude γ-methacryloxypropyltrimethoxysilane, followed by aging at 60° C. of 1 hour under agitation. As a result, a white precipitate was settled and was removed by filtration. 2 kg of the thus obtained γ-methacryloxypropyltrimethoxysilane and 6 g of 2,2'-methylenebis(4-ethyl-6-tert-butylphenol) serving as a polymerization inhibitor were subjected to distillation using a distillator equipped with a 3 liters reboiler and a 10 cm high, packed fractionator for about 4 hours to obtain purified γ-methacryloxypropyltrimethoxysilane.

COMPARATIVE EXAMPLE 1

The general procedure of Example 1 was repeated except that the steps of adding the neutralizing agent and aging at 60° C. for 1 hour under agitation were omitted, thereby obtaining purified γ-methacryloxypropyltrimethoxysilane.

EXAMPLE 2

The general procedure of Example 1 was repeated except that the white precipitate was not removed by filtration, thereby obtaining purified γ-methacryloxypropyltrimethoxysilane.

EXAMPLE 3

2 kg of crude γ-methacryloxypropyltrimethoxysilane obtained in the same manner as in Example 1 and 6 g of phenothiazine serving as a polymerization inhibitor were subjected to simple distillation over about 2 hours by the use of a distillator equipped with a 3 liters reboiler to obtain a γ-methacryloxypropyltrimethoxysilane fraction. 20 g of neutralizing agent B was added to the fraction, followed by aging at 60° C. for 1 hour under agitation to permit a white precipitate to settle. The thus neutralized fraction was distilled in the same manner as in Example 2 to obtain purified γ-methacryloxypropyltrimethoxysilane.

EXAMPLES 4 to 8

The general procedure of Example 1 was repeated except that there was used 20 g of each of neutralizing agents A, B', C, C' and C" instead of neutralizing agent B, thereby obtaining purified γ-methacryloxypropyltrimethoxysilane.

EXAMPLE 9

Trichlorosilane and allyl chloride were subjected to hydrosilylation reaction in a solvent in the presence of a platinum catalyst, followed by esterification reaction with methanol and urea and further by distillation to obtain γ-chloropropyltrimethoxysilane. The thus obtained γ-chloropropyltrimethoxysilane and potassium acrylate were subjected to desalting in a solvent, followed by removal of potassium chloride. Subsequently, low boiling components including the solvent were distilled off under reduced pressure to obtain crude γ-acryloxypropyltrimethoxysilane having a purity of approximately 90%.

Thereafter, the procedure of Example 1 was repeated except that 2 kg of the thus obtained crude γ-acryloxypropyltrimethoxysilane was used instead of γ-methacryloxypropyltrimethoxysilane of Example 1, thereby obtaining purified γ-acryloxypropyltrimethoxysilane.

COMPARATIVE EXAMPLES 2 TO 5

The general procedure of Example 1 was repeated except that 20 g of each of sodium carbonate, potassium acetate, pyridine and sodium methoxide was added instead of neutralizing agent B, thereby obtaining a purified γ-methacryloxypropyltrimethoxysilane product.

The distillation yield and purity of the respective purified alkoxysilanes obtained in Examples 1 to 9 and Comparative Examples 1 to 5 are summarized in Table. The purified alkoxysilanes were each subjected to measurements of electric conductivity ($C_E$) and pH of an extract with water, and a hydrolysis rate ($R_H$) according to the following procedures.

Electric Conductivity of Extract ($C_E$):

50 g of an alkoxysilane sample and 50 g of pure water were placed in a 100 ml polypropylene container and hermetically sealed, followed by shaking for 10 minutes and allowing to stand, thereby permitting the content to separate. The resultant aqueous phase was separated and taken out, followed by measurement of an electric conductivity at 25° C. by means of a conductivity measuring meter (CM-20E, available from Toa Denpa Ind. Co., Ltd.). It will be noted that the electric conductivity determined by a blank test using 100 g of pure water was 0.78 μS/cm.

pH of Extract:

The pH of the extract after completion of the measurement of the electric conductivity was measured at 25° C. by the use of a pH meter (HM-20B, available from Toa Denpa Ind. Co., Ltd.). It will be noted that the pH value by a blank test using pure water was 5.65.

Hydrolysis Rate ($R_H$):

20 g of an alkoxysilane sample and 5.0 g of n-decane serving as an internal standard substance were placed in a 100 ml polypropylene container and hermetically sealed, followed by shaking for 5 minutes and subjecting the content to measurement of a "prior" gas chromatogram. Thereafter, 50 g of pure water was added to the above-shaped mixture, followed by shaking for 2 hours and allowing to stand thereby causing the content to separate into phases. The resultant organic phase was subjected to measurement of an "post" gas chromatogram. The hydrolysis rate was calculated from the gas chromatograms determined prior to and after the shaking and the addition of the pure water according to the following equation.

Hydrolysis rate (%) = (A − B)/A × 100 wherein A = ("prior" peak area of the sample)/("prior" peak area of the internal standard substance)
wherein B = ("post" peak area of the sample)/("post" peak area of the internal standard substance)

The results are also shown in the Table below.

TABLE

| Sample No. | Alkoxysilane | Neutralizing Agent | Distillation Yield (%) | Purity (%) | $C_E$ ($\mu$S/cm) | pH (%) | $R_H$ |
|---|---|---|---|---|---|---|---|
| Ex. 1 | γ-methacryl-oxypropyltri-methoxysilane | B | 85.1 | 99.1 | 1.25 | 5.68 | 2.3 |
| Ex. 2 | γ-methacryl-oxypropyltri-methoxysilane | B | 86.7 | 98.2 | 2.02 | 5.66 | 3.6 |
| Ex. 3 | γ-methacryl-oxypropyltri-methoxysilane | B | 80.8 | 99.3 | 1.21 | 5.75 | 4.2 |
| Ex. 4 | γ-methacryl-oxypropyltri-methoxysilane | A | 84.3 | 98.4 | 3.13 | 5.74 | 5.2 |
| Ex. 5 | γ-methacryl-oxypropyltri-methoxysilane | B' | 82.8 | 97.5 | 2.87 | 5.79 | 4.9 |
| Ex. 6 | γ-methacryl-oxypropyltri-methoxysilane | C | 84.9 | 99.0 | 2.24 | 5.63 | 4.8 |
| Ex. 7 | γ-methacryl-oxypropyltri-methoxysilane | C' | 85.3 | 98.4 | 2.83 | 5.76 | 3.9 |
| Ex. 8 | γ-methacryl-oxypropyltri-methoxysilane | C" | 83.2 | 98.1 | 3.26 | 5.87 | 5.5 |
| Ex. 9 | γ-acryl-oxypropyltri-methoxysilane | B | 80.1 | 98.5 | 2.54 | 5.58 | 4.1 |
| Comp. Ex. 1 | γ-methacryl-oxypropyltri-methoxysilane | — | 89.8 | 98.9 | 14.50 | 5.23 | 27.9 |
| Comp. Ex. 2 | γ-methacryl-oxypropyltri-methoxysilane | sodium carbonate | 85.5 | 98.3 | 6.71 | 4.93 | 21.8 |
| Comp. Ex. 3 | γ-methacryl-oxypropyltri-methoxysilane | potassium acetate | 84.9 | 98.9 | 11.80 | 4.51 | 30.5 |
| Comp. Ex. 4 | γ-methacryl-oxypropyltri-methoxysilane | pyridine | 85.4 | 97.9 | 7.05 | 4.91 | 21.3 |
| Comp. Ex. 5 | γ-methacryl-oxypropyltri-methoxysilane | sodium methoxide | 58.9 | 85.7 | 12.10 | 5.11 | 28.9 |

As will be apparent from the above results, the contents of acidic impurities contained in the alkoxysilanes in small amounts can be reduced significantly as compared with those for comparison.

What is claimed is:

1. A process for removing acidic impurities from alkoxysilanes, which comprises:

providing an organic functional alkoxysilane of the following formula which contains small amounts of acidic impurities $$Y-R^1-Si(R^2)_{3-n}X_n$$

wherein Y represents an organic functional group, X represents an alkoxy group having from 1 to 4 carbon atoms, $R^1$ represents a divalent hydrocarbon group having from 1 to 11 carbon atoms, $R^2$ represents a monovalent hydrocarbon group having from 1 to 6 carbon atoms, and n is a value of 1, 2 or 3;

adding, to the alkoxysilane, at least one neutralizing agent selected from the group consisting of alkali metal salts of sterically hindered alcohols and alkali metal salts of sterically hindered amines until substantially all of the acidic impurities are neutralized; and subjecting the resulting mixture to distillation to remove the neutralized acidic impurities from the alkoxysilane to obtain a substantially acidic impurity-free alkoxysilane.

2. The process according to claim 1, wherein the alcohols and amines have the following formulas $$R^3-\underset{\underset{R^3}{|}}{\overset{\overset{R^3}{|}}{C}}-O-H \tag{a}$$

-continued

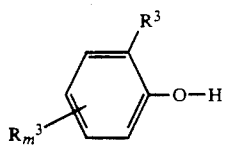
(b)

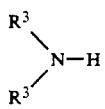
(c)

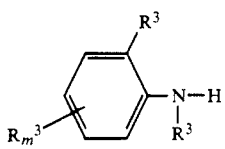
(d)

wherein R₃ may be the same or different and represent a monovalent hydrocarbon group having from 1 to 10 carbon atoms, and m is a value 0, 1, 2, 3 or 4.

3. The process according to claim 2, wherein the alcohols comprise at least one structure of the following formula

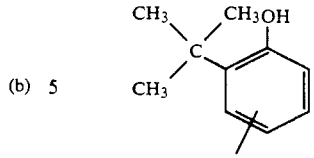

4. The process according to claim 2, wherein the amines comprise at least one structure of the following formula

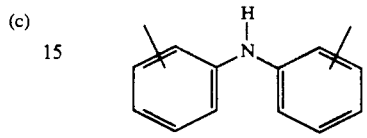

5. The process according to claim 1, wherein the organic functional alkoxysilane is obtained by esterification of a halogenosilane with an alcohol in a solvent.

6. The process according to claim 5, wherein the organic functional alkoxysilane obtained is subjected to crude distillation prior to adding said neutralizing agent.

7. The process according to claim 5, wherein the organic functional alkoxysilane obtained by the esterification in the solvent is directly neutralized with said neutralizing agent.

8. The process according to claim 7, wherein said neutralizing agent is added in an amount of 0.1 to 2 wt. %, based on the alkoxysilane ingredient, and agitated at a temperature of from room temperature to 80° C. for 1 to 2 hours.

9. The process according to claim 1, wherein said neutralizing agent is added in a stream of nitrogen.

10. The process according to claim 1, wherein Y is an acrylic group.

11. The process according to claim 1, wherein Y is a methacrylic group.

* * * * *